US00PP35688P2

(12) United States Plant Patent
Shim et al.

(10) Patent No.: US PP35,688 P2
(45) Date of Patent: Mar. 12, 2024

(54) ***HIBISCUS* PLANT NAMED 'WOOJEON'**

(50) Latin Name: *Hibiscus syriacus*
Varietal Denomination: Woojeon

(71) Applicants: Kyung-Ku Shim, Cheonan-si (KR); Ki-Byung Lim, Daegu (KR); Yoo-Mi Ha, Suwon-si (KR)

(72) Inventors: Kyung-Ku Shim, Cheonan-si (KR); Ki-Byung Lim, Daegu (KR); Yoo-Mi Ha, Suwon-si (KR)

( * ) Notice: Subject to any disclaimer, the term of this patent is extended or adjusted under 35 U.S.C. 154(b) by 0 days.

(21) Appl. No.: 18/218,037

(22) Filed: Jul. 4, 2023

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hibiscus* plant named 'Woojeon' that is characterized by its dwarf plant size, its floriferous habit with flowers on both the lateral and terminal branches, its short stem internodes, its flowers that are white in color with red centers, its narrowly shaped flower petals, its flowers that are long lasting on the plant, and its foliage that is dark in color, thick, narrow in size, and margins that are not strongly incised.

2 Drawing Sheets

Botanical classification: *Hibiscus syriacus.*
Cultivar designation: 'Woojeon'.

CROSS REFERENCE TO A RELATED APPLICATIONS

This application is related to a plant breeders' rights application in Republic of Korea filed on Feb. 12, 2015, application No. 2015-179 and European Community Plant Variety Office (CPVO) Plant Breeder's Rights filed on Jun. 1, 2023 Application No. 20231191. This application is also related to a U.S. Plant Patent Application filed for a plant derived from the same Inventor that is entitled *Hibiscus* Plant Named 'Samilhong' (U.S. Plant patent application Ser. No. 18/218,034).

BACKGROUND OF THE INVENTION

The present invention relates to a new and distinct cultivar of *Hibiscus syriacus* named 'Woojeon' and will be referred to hereafter by its cultivar name, 'Woojeon'. 'Woojeon' is a new cultivar of *Hibiscus* grown for use as a landscape and container plant.

The new cultivar was developed through an ongoing breeding program conducted by the Inventors in Cheonan-si, Chungcheongnam-do, Republic of Korea. The goal of the breeding program are to develop new cultivars of *Hibiscus* that exhibit very dwarf, compact, and floriferous plant habits, dense branching with short stem internodes, and flowers that last 3 days.

'Woojeon' arose from a cross made by the Inventors in 2008 between *Hibiscus syriacus* 'Andong' (not patented) as the female parent and *Hibiscus syriacus* 'Namwon' (not patented) as the male parent. 'Woojeon' was selected as a single unique plant from the resulting seedlings in 2014.

Asexual propagation of the new cultivar was first accomplished by the Inventors by stem cuttings in 2012 in Cheonan-si, Chungcheongnam-do, Republic of Korea. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Woojeon' as a new and distinct cultivar of *Hibiscus*.

1. 'Woojeon' exhibits a dwarf plant size.
2. 'Woojeon' exhibits a floriferous habit with flowers on both the lateral and terminal branches.
3. 'Woojeon' exhibits short stem internodes.
4. 'Woojeon' exhibits flowers that are white in color with red centers.
5. 'Woojeon' exhibits narrowly shaped flower petals.
6. 'Woojeon' exhibits flowers that are long lasting on the plant.
7. 'Woojeon' exhibits foliage that is dark in color, thick, narrow in size, and margins that are not strongly incised.

The female parent of 'Woojeon' differs from 'Woojeon' in having flowers that are smaller in size, flowers that last a shorter time, leaves that are smaller in size and lighter green in color, and a slightly more compact plant habit. The male parent of 'Woojeon' differs from 'Woojeon' in having flowers that are light pink in color with smaller red centers. 'Woojeon' can also be compared to in the *Hibiscus* cultivars 'Samilhong' and 'Antong Two' (U.S. Plant Pat. No. 19,547). 'Samilhong' is similar to 'Woojeon' in having a compact plant habit, long lasting flowers and short internodes. 'Samilhong' differs from 'Woojeon' in having flowers that are purple-pink in color, and leaves that are wider with margins that are more incised. 'Antong Two' is similar to 'Woojeon' in having flowers that are white in color with red centers. 'Antong Two' differs from 'Woojeon' in having a less compact plant habit, is less floriferous blooming habit, and leaves that are smaller in size.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by plantipp, nousbo, and Ko Noordman.

BRIEF DESCRIPTION OF THE DRAWINGS

The accompanying color photographs illustrate the overall appearance and distinct characteristics of the new *Hibiscus*. The photographs were taken of 3.5-year-old plants of 'Woojeon' as grown outdoors in a trial field in Boskoop, The Netherlands.

The photograph in FIG. 1 provides a side view of 'Woojeon' in bloom.

Figure 1:
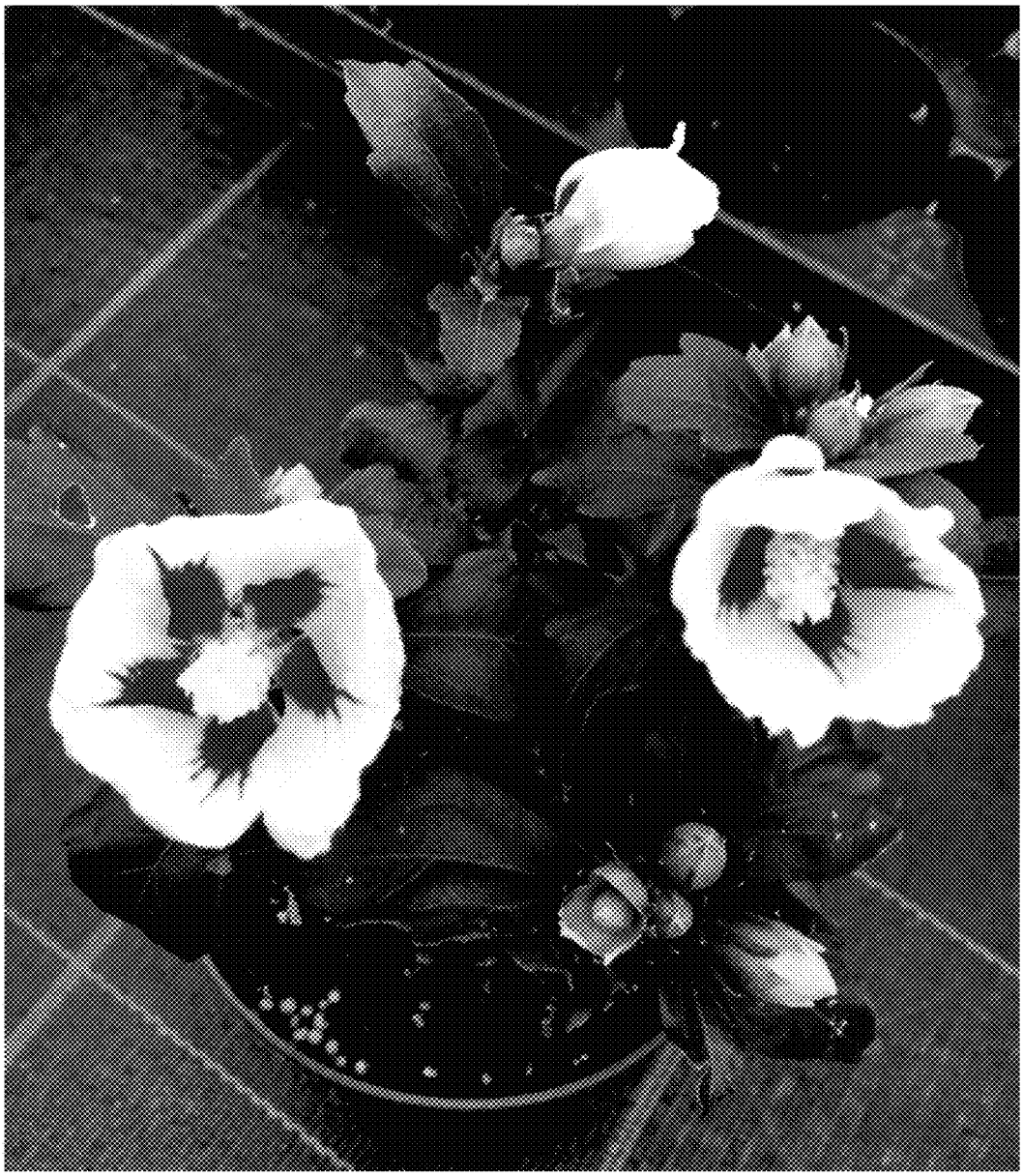
Figure 2:
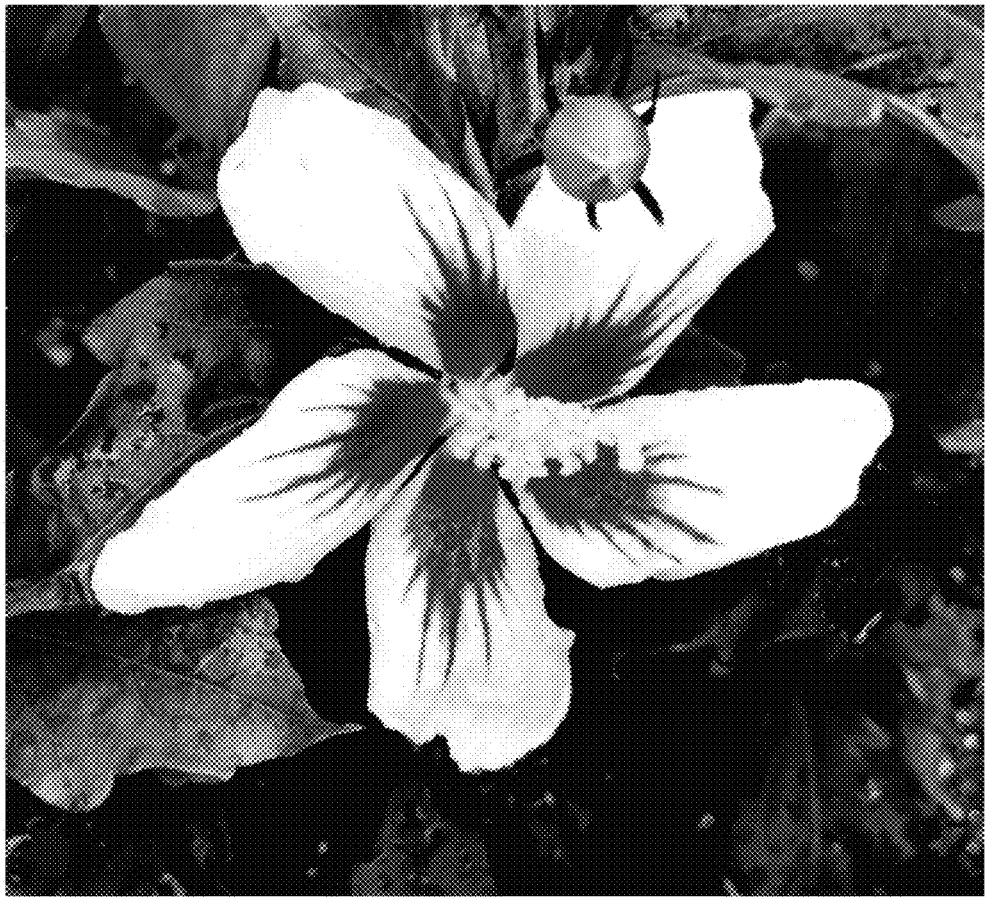

The photograph in FIG. 2 provides a close-up view of a flower of 'Woojeon'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 3.5-year-old plants of the new cultivar as grown outdoors in a trial field in Boskoop, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General characteristics:

- *Blooming period.*—Late July to early October in The Netherlands.
- *Plant type.*—Deciduous flowering shrub.
- *Plant habit.*—Dwarf, compact, freely branched.
- *Height and spread.*—An average of 55 cm in height and spread.
- *Hardiness.*—At least in U.S.D.A. Zones 5 to 9.
- *Diseases and pests.*—No susceptibility or resistance to disease or pests has been observed.
- *Root description.*—Fibrous roots, N155A in color.
- *Propagation.*—Stem cuttings.
- *Root development.*—Roots initiate in about 10 weeks from an unrooted cutting and fully root in a P9 container in one year (with overwintering).
- *Growth rate.*—Moderate.

Stem description:

- *Shape.*—Rounded.
- *Stem color.*—Young; 137B, mature wood; 197B, lenticels 199B.
- *Stem size.*—Main stem; 32 cm in length, 1.5 cm in diameter, lateral branches; average of 26 cm in length and 4 mm in width.
- *Stem surface.*—Young; sparsely pubescent, glossy, mature; woody, finely striated and rugose.
- *Stem aspect.*—Held in multiple angles.
- *Stem strength.*—Strong.
- *Branching.*—Main; 1, lateral; 29.
- *Internode.*—Average of 4.5 cm.

Foliage description:

- *Leaf shape.*—Ovate (3-lobed).
- *Leaf division.*—Simple.
- *Leaf base.*—Cuneate.
- *Leaf apex.*—Young; acute, mature; rounded.
- *Leaf venation.*—Palmate, young veins upper surface color; 137C, young veins lower surface color; 137C to 137D, mature veins upper surface; 139A to 139B, mature veins lower surface; 137B to 137C.
- *Leaf margins.*—Lobed.
- *Leaf attachment.*—Petiolate.
- *Leaf arrangement.*—Alternate.
- *Leaf aspect.*—Upward, cupped.
- *Leaf surface.*—Upper surface glabrous, lower surface very slightly pubescent.
- *Leaf color.*—Young upper surface; 143A, young lower surface; 143C, mature upper surface; 139A, mature lower surface; 137B.
- *Leaf size.*—An average of 7.6 cm in length and 5 cm in width.
- *Leaf quantity.*—An average of 16 per branch.
- *Petioles.*—An average of 1.8 cm in length and 2 mm in diameter, surfaces are both smooth and glabrous, upper surface 137B, lower surface 137B to 137C.

Flower description:

- *Inflorescence type.*—Flowers are solitary from upper leaf axils.
- *Lastingness of flowers.*—43 hours per flower, self-cleaning.
- *Flower size.*—An average of 9.1 cm in diameter.
- *Flower fragrance.*—None.
- *Flower shape.*—Rotate.
- *Flower number.*—Per lateral branch; average of 1 flowers, 8 buds.
- *Flower aspect.*—Slightly upright.
- *Flower bud.*—Ovate in shape, 1.3 cm in length, 7 mm in width, 138B in color.
- *Petals.*—5, obovate in shape, an average of 4.8 cm in length and 2.3 cm in width, irregularly incised, acute apex, base is attenuate, both surfaces glabrous, color; when opening and fully open upper and lower surface NN155D, center 59B.
- *Calyx.*—Campanulate in shape, average of 2 cm in length and 1 cm in diameter.
- *Epicalyx.*—Comprised of 6 bracts held upright surrounding sepals, lanceolate in shape, apiculate apex, truncate base, average of 1.8 cm in length and 5 mm in width, color of both surfaces 145A, both surfaces are glabrous and dull.
- *Sepals.*—5, fused, an average of 2 cm in length and 2 mm in width, color of both surfaces 137B, subulate in shape, acuminate apex, entire margins, both surfaces smooth and glabrous.

*Peduncles.*—An average of 4 mm in length and 2 mm in diameter, strong, 137A in color, pubescent.

*Pedicels.*—Not present, flowers are solitary from terminal leaf axils.

Reproductive organs:

*Gynoecium.*—Pistil; 1, 3.8 cm in length, stigmas; 5-parted, rounded in shape, 5 mm in diameter, 2 mm in depth, surface densely covered with short fuzzy hairs, 155A in color, styles; 3.2 cm in length, 0.7 mm in width, 155A in color, surface is glabrous and glossy, ovary; orbicular in shape with round apex, 1.8 cm in length, 4 mm width, 155A in color.

*Androecium.*—Stamens; average of 35, stamens are clustered and implanted into upper portion of style, anthers; round in shape, 3 mm in length, 2D in color, filament; 2 mm in length, color NN155D, pollen; abundant in quantity and 155A in color.

*Fruit/seeds.*—None observed to date.

It is claimed:

1. A new and distinct cultivar of *Hibiscus* plant named 'Woojeon' as herein illustrated and described.

* * * * *